United States Patent
Okamoto et al.

(10) Patent No.: US 8,586,067 B2
(45) Date of Patent: Nov. 19, 2013

(54) MICROBICIDAL AND ANTISEPTIC GEL COMPOSITION

(75) Inventors: Kazuki Okamoto, Osaka (JP); Tsuyoshi Miura, Osaka (JP); Manabu Soga, Osaka (JP); Yutaka Nishihara, Osaka (JP)

(73) Assignee: Maruishi Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 12/514,658

(22) PCT Filed: Nov. 14, 2007

(86) PCT No.: PCT/JP2007/072109
§ 371 (c)(1),
(2), (4) Date: Jun. 15, 2009

(87) PCT Pub. No.: WO2008/059885
PCT Pub. Date: May 22, 2008

(65) Prior Publication Data
US 2010/0028291 A1 Feb. 4, 2010

(30) Foreign Application Priority Data
Nov. 15, 2006 (JP) .................................. 2006-309375

(51) Int. Cl.
*A01N 25/34* (2006.01)
(52) U.S. Cl.
USPC .......................... 424/404; 424/405; 424/78.07
(58) Field of Classification Search
None
See application file for complete search history.

(56) References Cited

U.S. PATENT DOCUMENTS

| 5,502,181 A | 3/1996 | Kojima et al. |
|---|---|---|
| 5,750,579 A | 5/1998 | Kamishita et al. |
| 6,203,804 B1 * | 3/2001 | Murakado et al. ............. 424/401 |
| 6,432,415 B1 * | 8/2002 | Osborne et al. ............... 424/400 |
| 2005/0271595 A1 | 12/2005 | Brown |

FOREIGN PATENT DOCUMENTS

| JP | 6-199700 | 7/1994 |
|---|---|---|
| WO | 2006/085907 | 8/2006 |

OTHER PUBLICATIONS

Suzuki et al., "The effect of apparent molecular weight and components of agar on gel formation", 2001, Food Sci. Technol. Res., 7 (4), 280-284.*
International Search Report issued Jan. 8, 2008 in the International (PCT) Application of which the present application is the U.S. National Stage.
Extended European Search Report issued May 30, 2012 in corresponding European Application No. 07831839.1.

* cited by examiner

*Primary Examiner* — James Rogers
(74) *Attorney, Agent, or Firm* — Wenderoth, Lind & Ponack, L.L.P.

(57) ABSTRACT

A microbicidal and antiseptic composition, which comprises the following (a), (b) and (c):
  (a) at least one kind of alcohols selected from the group consisting of ethanol and isopropanol;
  (b) at least one kind of carboxyvinyl polymers selected from the group consisting of polyacrylic acids, polyacrylates, copolymers of polyacrylic acids and polyacrylic acid alkyl esters, and copolymers of polyacrylates and polyacrylic acid alkyl esters; and
  (c) agar.

14 Claims, 1 Drawing Sheet

MICROBICIDAL AND ANTISEPTIC GEL COMPOSITION

This application is a U.S. national stage of International Application No. PCT/JP2007/072109 filed Nov. 14, 2007.

TECHNICAL FIELD

The present invention relates to a microbicidal and antiseptic gel composition used for hand disinfection etc.

BACKGROUND ART

A microbicidal and antiseptic agent used in hospitals etc. may be a viscous gel composition obtained by adding a thickener to a microbicide solution for the purpose of preventing the agent from spilling when taken on the palm or dripping down when rubbed into the hand.

For example, JP-B-7-29884 and JP-A-11-9667 describe microbicidal and antiseptic agents obtained by adding a carboxyvinyl polymer as a thickener to an alcoholic solution. Also, Japanese Patent Nos. 3499882, 2533723 and 3456236 describe microbicidal and antiseptic agents obtained by adding a carboxyvinyl polymer and a cellulosic polymer compound as thickeners to an alcoholic solution.

However, these thickeners cannot sufficiently increase the viscosity of the composition when the alcohol concentration is high, and adding increased amounts of thickeners for higher viscosity causes twisted semisolid of the composition when applied to the hand. Also, antiseptic agents with these thickeners are sticky and uncomfortable when used.

Meanwhile, JP-A-2000-86408 describes a microbicidal and antiseptic gel agent comprising an alcoholic solution, a resin polymer such as a carboxyvinyl polymer and glucomannan. When the microbicidal and antiseptic agent is rubbed into the hand, as the agent loses its water, the glucomannan component becomes a rubbery material and is left as a residue like twisted thin paper strings. Dirt on the hand is attached to the residue and, as a result, removed. The document also describes that agar and/or a cellulosic derivative may be added in order to enhance the effect of the gel composition. However, since this microbicidal and antiseptic agent leaves a residue composed of glucomannan after rubbed into the hand, dry touch cannot be obtained.

In addition, Japanese Patent No. 3531735 describes a microgel that can be used as a thickener. The microgel with an average particle size of 0.1 to 1 μm is obtained by dissolving a hydrophilic compound having gelation ability such as agar in water, cooling the solution for gel formation, and then pulverizing the gel. It is said that a composition to which the above-mentioned microgel thickener is added is not sticky and that the viscosity thereof does not decrease even when a large amount of pharmaceutical components or salts are comprised. The microgel thickener is expensive since it is produced by a complicated method.

SUMMARY OF INVENTION

Technical Problem

The object of the present invention is to provide a microbicidal and antiseptic composition having sufficient viscosity and dry touch.

Solution to Problem

The present inventors made extensive examination to solve the problem described above, and found that a microbicidal and antiseptic composition comprising:

(a) at least an alcohol selected from the group consisting of ethanol and isopropanol;
(b) at least a carboxyvinyl polymer selected from the group consisting of a polyacrylic acid, a polyacrylate, a copolymer of a polyacrylic acid and a polyacrylic acid alkyl ester, and a copolymer of a polyacrylate and a polyacrylic acid alkyl ester; and
(c) agar;

has practically sufficient viscosity even when comprising high concentration of alcohol. The present inventors also found that this composition, when applied onto the hand, spreads well, is free from graininess, and leaves not stickiness but comfortable feel with dry touch. Further, the present inventors found that this composition has an excellent moisturizing effect.

The present invention, which has been completed based on the above-mentioned findings, provides the following microbicidal and antiseptic compositions.

(1) A microbicidal and antiseptic composition, which comprises the following (a), (b) and (c):
(a) at least an alcohol selected from the group consisting of ethanol and isopropanol;
(b) at least a carboxyvinyl polymer selected from the group consisting of a polyacrylic acid, a polyacrylate, a copolymer of a polyacrylic acid and a polyacrylic acid alkyl ester, and a copolymer of a polyacrylate and a polyacrylic acid alkyl ester; and
(c) agar.

(2) The microbicidal and antiseptic composition according to the above-mentioned (1), wherein the content percentage of alcohol relative to the whole composition is 40 to 95% (v/v).

(3) The microbicidal and antiseptic composition according to the above-mentioned (1) or (2), wherein the agar is a low-strength agar composed of molecules shorter than those of natural agar.

(4) The microbicidal and antiseptic composition according to the above-mentioned (3), wherein the low-strength agar has a jelly strength of 10 to 250 g/cm$^2$ as measured in a gel state at a concentration of 1.5% (w/w).

(5) The microbicidal and antiseptic composition according to the above-mentioned (3), wherein the low-strength agar is the one obtained by cleaving the molecules of natural agar by acid treatment, alkali treatment or heat treatment.

(6) The microbicidal and antiseptic composition according to anyone of the above-mentioned (1) to (5), wherein the agar content relative to the whole composition is 0.05 to 5% (w/v).

(7) The microbicidal and antiseptic composition according to any one of the above-mentioned (1) to (6), wherein the carboxyvinyl polymer content relative to the whole composition is 0.01 to 4% (w/v).

(8) The microbicidal and antiseptic composition according to anyone of the above-mentioned (1) to (7), which further comprises at least one kind selected from the group consisting of cellulose and a cellulose derivative.

(9) The microbicidal and antiseptic composition according to any one of the above-mentioned (1) to (8), which further comprises at least one kind selected from the group consisting of higher aliphatic alcohols having 12 to 22 carbon atoms.

(10) A microbicidal and antiseptic method, which comprises applying the composition according to any one of the above-mentioned (1) to (9) to a hand.

(11) A use of the composition according to any one of the above-mentioned (1) to (9), as a microbicidal and antiseptic agent.

Advantageous Effects of Invention

The microbicidal and antiseptic composition of the present invention is characterized by comprising a carboxyvinyl polymer and agar as thickeners. Thereby, even when comprising high concentration of alcohol, the composition of the present invention is resistant to dripping because of its high viscosity. Also, the composition of the present invention spreads smoothly without graininess when applied onto the hand, and leaves not stickiness or pasty feel but dry touch after dried.

Generally, a microbicidal and antiseptic agent comprising high concentration of alcohol may cause hospital staff members who use the agent many times daily to suffer from rough, cracked hands. If the cracked hand catches bacterial infection, a serious problem of hospital infection may occur. In order to avoid such hand roughness, moisturizers, such as glycerol and propyleneglycol, had to be added. In contrast, the microbicidal and antiseptic composition of the present invention, which comprises a carboxyvinyl polymer and agar as thickeners and does not comprise any other moisturizer, gives less alcohol-formulation-specific dryness, has an excellent moisturizing effect, and hardly causes rough skin.

DESCRIPTION OF EMBODIMENTS

Figure 1:
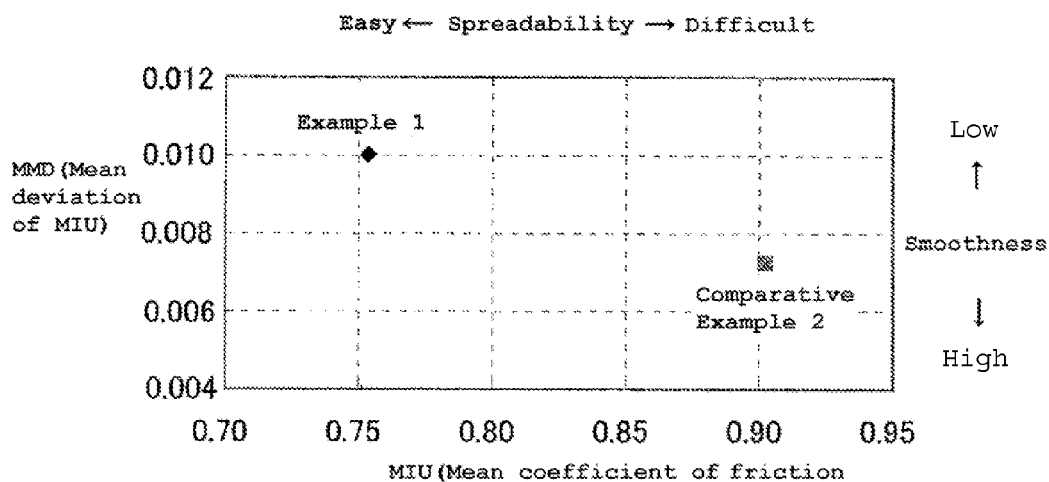
FIG. 1 is a graph showing the comparison results of mean coefficient of friction (MIU) and mean deviation of MIU (MMD) between compositions of Example 1 and Comparative Example 2.

Hereinafter, the present invention will be described in detail.

The microbicidal and antiseptic composition of the present invention is characterized by comprising the following (a), (b) and (c):

(a) at least an alcohol selected from the group consisting of ethanol and isopropanol;

(b) at least a carboxyvinyl polymer selected from the group consisting of a polyacrylic acid, a polyacrylate, a copolymer of a polyacrylic acid and a polyacrylic acid alkyl ester, and a copolymer of a polyacrylate and a polyacrylic acid alkyl ester; and (c) agar.

Alcohol

The alcohol as a microbicidal component may be ethanol, isopropanol or a combination thereof. In particular, ethanol is preferred.

The content percentage of alcohol relative to the whole composition is preferably about 40 to 95% (v/v), more preferably about 50 to 85% (v/v), and still more preferably about 60 to 85% (v/v). When the alcohol content is within the above-mentioned range, sufficient microbicidal power can be obtained. Also, an alcohol content within the above-mentioned range does not cause rough skin and allows other components to dissolve well.

Carboxyvinyl Polymer

The composition of the present invention comprises a carboxyvinyl polymer, and thereby has viscosity and prevents agar from depositing even with high concentration of alcohol. The carboxyvinyl polymer to be used may be one or more kinds of polymers selected from the group consisting of a polyacrylic acid, a polyacrylate, a copolymer of a polyacrylic acid and a polyacrylic acid alkyl ester, and a copolymer of a polyacrylate and a polyacrylic acid alkyl ester.

Even when a polyacrylic acid is used at the time of mixing of each component, if alkali is added as described below to adjust pH, a part or all of the polyacrylic acid may have been changed to a polyacrylate in the resulting composition. Preferred is using a low-viscosity polyacrylic acid when an alcohol, a carboxyvinyl polymer and agar are mixed, and then changing a part or all of the polyacrylic acid to a polyacrylate by pH adjustment in order to raise the viscosity. Using a polyacrylate from the time of mixing is also preferred.

Examples of the polyacrylate include a polyacrylic acid; an alkali metal salt such as a sodium salt and a potassium salt of a polyacrylic acid; an amine salt such as a monoethanolamine salt, a diethanolamine salt and a triethanolamine salt of a polyacrylic acid; an ammonium salt of a polyacrylic acid; etc. Inter alia, alkali metal salts are preferred.

Examples of the polyacrylic acid alkyl ester include poly(methyl acrylate), poly(ethyl acrylate) and poly(propyl acrylate).

The polyacrylic acid may be cross-linked or non cross-linked, and a cross-linked polymer is preferred because of its high thickening effect.

The content percentage of carboxyvinyl polymer relative to the whole composition is preferably about 0.01 to 4% (w/v), more preferably about 0.01 to 2% (w/v), and still more preferably about 0.1 to 1% (w/v). When the carboxyvinyl polymer content is within the above-mentioned range, a microbicidal and antiseptic composition having sufficient viscosity and comfortable feel can be obtained. In addition, separation of agar in high concentration of alcohol can be prevented.

Agar

In the present invention, combinational use of a carboxyvinyl polymer and agar as thickeners can provide a composition comprising an alcoholic microbicide with practically sufficient viscosity, comfortable feel without pasty feel, and moisturizing effect.

Agar is a viscous substance extracted from seaweed, such as red algae. In the present invention, publicly known agar can be used without restriction. Agar is commercially available in powder form, flake form, etc.

The jelly strength of agar in a gel state varies depending on the length of constituent molecules. In the present invention, agar extracted from seaweed having natural molecular structure may be used as it is; however, a low-strength agar composed of molecules shorter than those of natural agar is preferably used. By using low-strength agar, better dry touch and better moisturizing effect as well as smooth feel without graininess can be obtained.

Inter alia, a low-strength agar having a jelly strength of about 10 to 250 $g/cm^2$ as measured in a gel state at an agar concentration of 1.5% (w/w) is preferred. When the jelly strength is within the above-mentioned range, the effect of using a low-strength agar is guaranteed while sufficient viscosity of the composition is maintained.

In the present invention, the jelly strength is measured with a Nikkansui-method (a method used in Japan Agar Marine Industry Union) jelly strength tester, specifically in the manner described in Examples.

However, a jelly strength of 100 g/cm or less was practically determined using the proportional relation between jelly strength and agar concentration because such a low strength cannot be measured by the Nikkansui method. For example, the jelly strength of a gel comprising 1.5% (w/w) of agar is assumed to be 1/10 of the measured jelly strength of a gel comprising 15% (w/w) of agar.

A low-strength agar having a jelly strength of about 10 to 250 g/cm² as measured in a gel state at an agar concentration of 1.5% (w/w) can be obtained by, for example, cleaving molecules of natural agar by acid treatment, usually followed by neutralization with alkali. Publicly known acid and alkali can be used without restriction. Examples of the publicly known acid include sulfuric acid, hydrochloric acid, acetic acid, citric acid, etc., and examples of the publicly known alkali include sodium hydroxide, sodium carbonate, potassium phosphate, etc. The jelly strength can be adjusted by controlling acid usage, acid treatment time, and acid treatment temperature. A low-strength agar having the above-mentioned jelly strength can be produced according to the method described in Japanese Patent No. 3023244.

Alternatively, a low-strength agar having a jelly strength of about 10 to 250 g/cm² as measured in a gel state at an agar concentration of 1.5% (w/w) can be obtained by cleaving molecules of natural agar by heat treatment. Such agar can be obtained by, for example, a method comprising the steps of:

extracting an agar component from seaweed as raw material;

filtering the obtained extract;

turning the obtained filtrate into a gel and then dehydrating the obtained gel;

drying the obtained concentrated gel; and cleaving agar molecules by heat treatment after any one of the above steps. The step of heat treatment may be performed using an extruder under conditions where the die plate temperature is about 90 to 180° C. and the pressure is about 7 to 15 MPa. The step of heat treatment is preferably performed after the drying step, with the use of milled dry agar to which water has been added to put it into a wet state. A low-strength agar having the above-mentioned jelly strength can be produced, in particular, according to the method described in JP-A-10-146174.

A low-strength agar having the above-mentioned jelly strength is marketed by Ina Food Industry under the name of "Ultra Agar".

A low-strength agar having the following rheological properties in a compressed mode of the agar gel is also preferred: the stress at a shear rate of 0.005 (1/s) and at the time of 20% deformation is 20,000 Pa or more, and the stress relaxation time needed until the stress becomes half the initial stress is 8 seconds or more.

A low-strength agar having such stress and stress relaxation time can be produced by, for example, treating raw seaweed with alkali to a degree adjusted depending on the amount of comprised sulfate radical, washing the treated material with water to sufficiently clear the alkali, extracting and filtering an agar component with near-neutral hot water, turning it into a gel, and then dehydrating and drying. The alkali treatment is performed using a treatment solution selected from caustic soda, caustic potash, slaked lime, quicklime, and ammonium hydroxide, and the treatment degree may be adjusted within the range of treatment solution concentration of about 0.1 to 10.0%, treatment temperature of about 0 to 100° C., and treatment time of about 1 to 180 minutes. When raw seaweed comprising 1 to 10% of sulfate radical is used, a low-strength agar having the above-mentioned stress and stress relaxation time can be obtained by extraction with neutral hot water, without alkali treatment of raw seaweed and acid treatment after extraction. In this case, a transparent gel can be obtained because neither alkali treatment nor acid treatment is performed. A low-strength agar having the above-mentioned stress and stress relaxation time can be produced, in particular, according to the method described in JP-A-2000-157225.

A low-strength agar having the above-mentioned stress and stress relaxation time is marketed by Ina Food Industry under the name of "Ultra Agar".

The content percentage of agar relative to the whole composition is preferably about 0.05 to 5% (w/v), more preferably about 0.01 to 1% (w/v), and still more preferably about 0.1 to 11 (w/v). When the content is within the above-mentioned range, the above-mentioned effect of using agar is guaranteed while slimy feel specific to agar is avoided.

Higher Aliphatic Alcohols

The composition of the present invention preferably comprises a linear or branched higher aliphatic alcohol having 12 to 22 carbon atoms. A composition comprising such a higher aliphatic alcohol spreads further smoothly when hands are rubbed together, and leaves further dry touch after being dried. Even at the moment of drying, the composition gives neither frictional nor scratchy feel.

The linear or branched higher aliphatic alcohol more preferably has 12 to 20 carbon atoms, and still more preferably has 14 to 18 carbon atoms. Those having even numbers of carbon atoms are preferred because they occur in nature and therefore are easy to obtain. Also, saturated alcohols are preferred to unsaturated alcohols that have a characteristic odor.

Examples of linear saturated aliphatic alcohols having 12 to 22 carbon atoms include lauryl alcohol (C12), tridecyl alcohol (C13), myristyl alcohol (C14), pentadecyl alcohol (C15), cetyl alcohol (C16), heptadecyl alcohol (C17), stearyl alcohol (C18), nonadecyl alcohol (C19), arachyl alcohol (C20), behenyl alcohol (C22), etc.

The higher aliphatic alcohols having 12 to 22 carbon atoms may be used alone or in a combination of two or more kinds.

When such a higher aliphatic alcohol is comprised, the content percentage relative to the whole composition is preferably about 0.01 to 1% (w/v), and more preferably about 0.1 to 0.5% (w/v). When the content is within the above-mentioned range, the above-mentioned effect of using a higher aliphatic alcohol is guaranteed while sticky feel specific to higher aliphatic alcohols is avoided.

Auxiliary Thickeners

Other auxiliary thickeners may be comprised in the composition of the present invention as long as they do not spoil the effect of the present invention. Examples of other thickeners include cellulose; cellulose derivatives, such as hydroxyethyl cellulose, hydroxypropyl cellulose, hydroxypropylmethyl cellulose, hydrophobized hydroxypropylmethyl cellulose, methyl cellulose, carboxymethyl cellulose sodium; copolymers having acrylic acid or a salt thereof as a constituent, such as cross-linked acrylic acid-starch graft copolymer and N-vinylacetamide/sodium acrylate copolymer; polyvinyl alcohol; polyvinyl pyrrolidone; polyethylene oxide; methyl vinyl ether/maleic anhydride copolymer; polyacrylamide; alginic acid; sodium alginate; propylene glycol alginate; gelatin; gum arabic; gum tragacanth; locust bean gum; guar gum; tamarind gum; xanthan gum; gellant gum; carrageenan, etc. The auxiliary thickeners may be used alone or in a combination of two or more kinds.

In particular, an auxiliary thickener selected from a group consisting of cellulose and cellulose derivatives is preferred, and hydroxyethyl cellulose, hydroxypropyl cellulose, hydroxypropylethyl cellulose, and hydrophobized hydroxypropylethyl cellulose are more preferred. The microbicidal and antiseptic composition of the present invention comprises cellulose and/or a cellulose derivative in addition to a carboxyvinyl polymer and agar, and thereby the carboxyvinyl polymer content can be reduced.

When an auxiliary thickener is comprised, the content percentage varies depending on the kind thereof. When cellulose and/or a cellulose derivative is comprised, the amount to be used is, to the whole composition, preferably about 0.001 to 1% (w/v), and more preferably about 0.01 to 0.1%. When the content is within the above-mentioned range, the above-mentioned effect of using cellulose and/or a cellulose derivative is guaranteed while twisted semisolid specific to cellulose and/or cellulose derivatives is avoided.

PH Adjustor

The composition of the present invention preferably has a pH of about 4 to 9 for thickening a carboxyvinyl polymer. For this reason, a pH adjustor may be comprised in the composition of the present invention as needed. The pH adjustor may be any agent as long as it is suitable for skin external use, such as drugs and cosmetics, and is not particularly limited. Examples of such pH adjustors include alkali metal hydroxides such as sodium hydroxide and potassium hydroxide; hydroxides of ammonium such as ammonium hydroxide; alkanolamines such as monoethanolamine, diethanolamine, triethanolamine, monoisopropanolamine, diisopropanolamine and triisopropanolamine; alkylamines such as 2-amino-2-methyl-1-propanol and 2-amino-2-methyl-1,3-propanediol; basic amino acids such as lysine and arginine; POE alkylamines; etc. Inter alia, an alkanolamine is preferred and diisopropanolamine is more preferred because of high solubility in alcohol.

Also, organic acids or organic acid salts, such as citric acid, tartaric acid, lactic acid, glycolic acid, malic acid, salicylic acid, fumaric acid, methanesulfonic acid, maleic acid, acetic acid, and disodium EDTA; or inorganic acids, such as hydrochloric acid, phosphoric acid, sulfuric acid, nitric acid, hydrobromic acid; etc. can be used as needed.

The pH adjustors may be used alone or in a combination of two or more kinds.

Other Components

Additional microbicidal and antiseptic agent may be comprised in the composition of the present invention as long as it does not spoil the effect of the present invention. Examples of such a microbicidal and antiseptic agent include acrinol, benzethonium chloride, benzalkonium chloride, benzalkonium cetyl phosphate, cetylpyridinium chloride, methylrosanilinium chloride, iodine, potassium iodide, iodophors such as povidone iodine, iodoform, mercurochrome, alkylpolyamino ethylglycine, thimerosal, bronopol, resorcinol, hinokitiol, triclosan, phenol and derivatives thereof, chlorhexidine salts such as chlorhexidine glyconate, chlorhexidine acetate, and chlorhexidine hydrochloride, etc.

The composition of the present invention does not need to comprise a moisturizer, but may comprise a publicly known moisturizer added to microbicidal and antiseptic agents. Examples of such moisturizers include, for example, silicone oil, fatty acid ester, pyrrolidone carboxylate, sodium pyrrolidone carboxylate, sodium lactate, hyaluronic acid, sodium hyaluronate, sodium dl-pyrrolidone carboxylate, urea, propylene glycol, glycerol, etc. Examples of the silicone oil include dimethyl silicone oil, methylphenyl silicone oil, methyl hydrogen silicone oil, etc. Silicone oil has, in addition to moisturizing action, a lubrication action that can make it easy to put on or take off surgical gloves. Examples of the fatty acid ester include isopropyl myristate, isopropyl palmitate, isopropyl stearate, isobutyl oleate, isobutyl maleate, etc.

The composition of the present invention may comprise a drug such as glycyrrhizic acid or a derivative thereof, vitamin E, vitamin-E acetate, and vitamin $B_6$; a nonionic surfactant; an amino acid or a derivative thereof; diisobutyl adipate; allantoin, etc.

The composition of the present invention is dried without being washed away after being applied to the hand, and therefore preferably free from any component that does not uniformly mix with water or alcohol, for example, glucomannan.

Preparation Method

The composition of the present invention can be obtained by mixing each component, heating the mixture to dissolve agar and possibly other components that are in a solid state at room temperature, such as a higher aliphatic alcohol etc., and then usually adjusting the pH.

Method for Use

The hand can be sterilized or disinfected by applying the above-described composition of the present invention to the hand or by further rubbing it into the hand. That is, the present invention also includes a use of the above-described composition of the present invention as a microbicidal and antiseptic agent. The amount used at a time may be an adequate amount (for example, about 0.5 to 3 mL). The number of times to use the composition daily is not particularly limited, and it may be applied to or further rubbed into the hand as needed.

EXAMPLES

Hereinafter, the present invention will be described in more detail by Examples and Test Examples, but it is not limited thereto.

(1) Preparation of Microbicidal and Antiseptic Compositions

Each component shown in Table 1 below was successively blended with stirring to prepare 100 mL of each composition. Agar was dissolved in hot water at around 90° C., cooled with stirring, and then blended. Carbopol Ultrez 10 made by Noveon was used as a carboxyvinyl polymer. Low-strength agar AX-30 by Ina Food Industry was used as agar. The jelly strength of this low-strength agar in a gel state at a concentration of 1.5% (w/w) was about 30 g/cm². The jelly strength was determined by preparing a 1.5% (w/w) aqueous solution of agar, boiling it, leaving it to cool at 20° C. for 15 hours for gelation, and then measuring the maximum load per $cm^2$ applied to the surface of the obtained gel without causing any collapse thereof for 20 seconds.

TABLE 1

|  | Example 1 | Example 2 | Example 3 | Example 4 | Example 5 | Comparative Example 1 |
|---|---|---|---|---|---|---|
| 93% (v/v) Ethanol | 83 mL<br>78.9% (v/v) | 83 mL<br>78.9 (v/v) | 83 mL<br>78.9% (v/v) | 83 mL<br>78.9% (v/v) | 67 mL<br>63.7% (v/v) | 83 mL<br>78.9% (v/v) |
| Carboxyvinyl polymer | 0.25 g<br>0.25% (w/v) | 0.2 g<br>0.2% (w/v) | 0.2 g<br>0.2% (w/v) | 0.2 g<br>0.2% (w/v) | 0.25 g<br>0.25% (w/v) | 0.25 g<br>0.25% (w/v) |
| Hydroxypropyl cellulose | 0.05 g<br>0.05% (w/v) | 0.05 g<br>0.05% (w/v) | 0.05 g<br>0.05% (w/v) |  | 0.05 g<br>0.05% (w/v) | 0.05 g<br>0.05% (w/v) |
| Hydroxyethyl cellulose |  |  |  | 0.02 g<br>0.02% (w/v) |  |  |
| Agar | 0.2 g | 0.2 g | 0.2 g | 0.2 g | 0.2 g |  |

TABLE 1-continued

|  | Example 1 | Example 2 | Example 3 | Example 4 | Example 5 | Comparative Example 1 |
|---|---|---|---|---|---|---|
| Cetanol | 0.2% (w/v) 0.15 g 0.15% (w/v) | 0.2% (w/v) | 0.2% (w/v) | 0.2% (w/v) | 0.2% (w/v) |  |
| Diisopropanolamine | 0.25 g 0.25% (w/v) | 0.2 g 0.2% (w/v) |  | 0.2 g 0.2% (w/v) | 0.2 g 0.2% (w/v) | 0.3 g 0.3% (w/v) |
| Triisopropanolamine |  |  | 0.2 g 0.2% (w/v) |  |  |  |
| Purified water | q.s. | q.s. | q.s. | q.s. | q.s. | q.s. |

(The weight of each component is shown in the upper line, and the content percentage relative to the whole composition is in the lower line.)

In the following Test Examples, GOJO MHS by GOJO Japan, which is a representative example of conventional microbicidal and antiseptic agents, was also used (Comparative Example 2). GOJO MHS is an aqueous solution comprising ethanol, a carboxyvinyl polymer, isopropyl myristate, and propylene glycol.

(2) Evaluation of Liquid Dripping

An adequate amount (size of a 500-yen coin) of each microbicidal and antiseptic composition of Example 1 and Comparative Example 2 (GOJO MHS) was put on a hand, rubbed into the entire hands, and then dried. Each panelist performed this action 5 times daily, and evaluated the liquid dripping on a 3-point scale of "dripping", "dripping a little", and "not dripping". The numbers of panelists were 31 for the composition of Example 1, and 30 for the composition of Comparative Example 2. The following Table 2 shows the percentages of panelists who made each evaluation.

TABLE 2

|  | Dripping | Dripping a little | Not dripping |
|---|---|---|---|
| Example 1 | 0.0% | 38.7% | 61.3% |
| Comparative Example 2 | 23.3% | 56.7% | 20.0% |

Table 2 indicates that the composition comprising agar in addition to a carboxyvinyl polymer as thickeners dripped less than the composition comprising only a carboxyvinyl polymer as a thickener.

(3) Evaluation of Feel in Use
(3-1) Evaluation of Sticky Feel and Dryness

Each panelist used the compositions of Example 1 and Comparative Example 2 (GOJO MHS) in the same manner as in the above-described evaluation of liquid dripping, and evaluated the state after each composition dried. The evaluation was made on a 3-point scale of "sticky or dry", "somewhat sticky or dry", and "good". The numbers of panelists were 31 for the composition of Example 1, and 30 for the composition of Comparative Example 2. The following Table 3 shows the percentages of panelists who made each evaluation.

TABLE 3

|  | Sticky or dry | Somewhat sticky or dry | Good |
|---|---|---|---|
| Example 1 | 0.0% | 13.3% | 86.7% |
| Comparative Example 2 | 0.0% | 23.3% | 76.7% |

Table 3 indicates that the composition comprising agar in addition to a carboxyvinyl polymer as thickeners gave less sticky feel or dryness than the composition comprising only a carboxyvinyl polymer as a thickener.

(3-2) Evaluation of Sticky Feel and Grainy Feel

Each panelist used the compositions of Examples 1 to 5 and Comparative Example 1 in the same manner as in the above-described evaluation of liquid dripping, and evaluated the state after each composition dried on a 3-point scale of "sticky or grainy", "somewhat sticky or grainy", and "not sticky or grainy". The number of panelists was 2. The results are shown in Table 4 below.

TABLE 4

|  | Sticky or grainy feel |
|---|---|
| Example 1 | Very good |
| Example 2 | Good |
| Example 3 | Good |
| Example 4 | Good |
| Example 5 | Good |
| Comparative Example 1 | Poor |

Very good: Not sticky or grainy
Good: Somewhat sticky or grainy
Poor: Sticky or grainy Table 4 indicates that the composition comprising agar in addition to a carboxyvinyl polymer and a cellulosic compound gave less sticky feel or grainy feel than the composition comprising only a carboxyvinyl polymer and a cellulosic compound as thickeners. The table also indicates that comprising cetanol further suppressed sticky feel or grainy feel.

(3-3) Evaluation of Smoothness

Each composition of Example 1 and Comparative Example 2 were measured for mean coefficient of friction (MIU) and mean deviation of MIU (MMD). MIU is associated with "ease of sliding" or "ease of spreading" which a person feels when rubbing the surface of a body. The higher this value, the harder the sliding or spreading. MMD is associated with "smoothness" which a person feels when rubbing the surface of a body. The lower this value, the greater the smoothness.

Specifically, 50 μL of each composition was applied onto the surface of an artificial leather strip set on the sample table of a friction tester (KES-SE by KATO TECH). On the artificial leather strip, a friction sensor made of silicone with a static load of 50 g was placed and made to slide at a speed of 1 mm/s, for determination of the friction resistance of the initial 3 cm slide. The measurement was performed in the environment at a temperature of 22.6° C. and with a relative humidity of 40.5%.

MIU was calculated by multiplying the integrated value of the friction resistance measured with the silicone friction sensor by a coefficient of 0.1, and MMD was calculated by multiplying the integral of the deviation of friction resistance detected with the silicone friction sensor by a coefficient of 0.01. Specifically, calculations were made by data processing by using the KES-FB SYSTEM data measurement program.

The results are shown in Table 5 and FIG. 1 below.

TABLE 5

|  | MIU (Difficulty of sliding and spreading) | MMD (Smoothness) |
|---|---|---|
| Example 1 | 0.7573 | 0.0103 |
| Comparative Example 2 | 0.9025 | 0.0074 |

Table 5 and FIG.1 indicate that the composition comprising agar in addition to a carboxyvinyl polymer as thickeners spread better than the composition comprising only a carboxyvinyl polymer as a thickener.

(4) Evaluation of Moisturizing Effect

Each of 8 panelists applied 100 μL of each composition of Example 1 and Comparative Example 2 (GOJO MHS) to their arm, left it for 30 minutes, dripped 10 μL of purified water, and wiped it off in 30 seconds. The stratum corneum was measured for its water content immediately, and 30 seconds, 60 seconds, 90 seconds, and 120 seconds after the wipe. The water content of the stratum corneum was determined using a skin surface hygrometer (SKICON-200EX by IBS). The percentage (skin water-holding capacity) of the mean value of the water contents at 30 seconds, 60 seconds, 90 seconds, and 120 seconds relative to the water content immediately after the wipe with purified water was calculated. The more the water retention, the better the moisturizing effect.

The results are shown in Table 6 and FIG. 2 below.

TABLE 6

| | Skin water-holding capacity (%) | | | | | | | |
|---|---|---|---|---|---|---|---|---|
| | Panelist | | | | | | | |
| | No. 1 | No. 2 | No. 3 | No. 4 | No. 5 | No. 6 | No. 7 | No. 8 |
| Example 1 | 14.7 | 14.1 | 19.4 | 13 | 10.9 | 13.9 | 12.1 | 11.2 |
| Comparative Example 2 | 11.7 | 11.4 | 15.4 | 14.5 | 9.1 | 10.4 | 10.5 | 9.4 |

Figure 2:
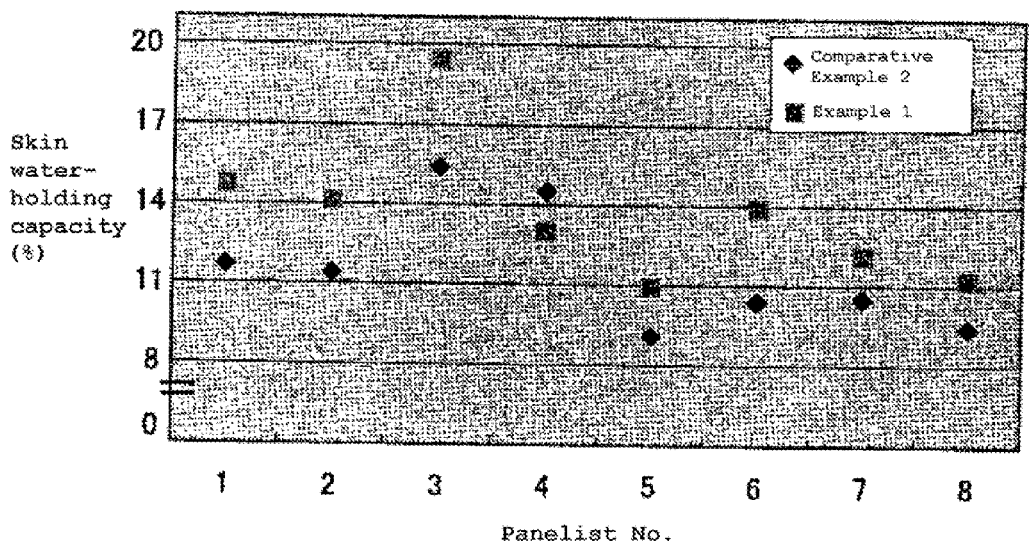
FIG. 2 is a graph showing the comparison results of water content in the stratum corneum between compositions of Example 1 and Comparative Example 2.

Table 6 and FIG. 2 indicate that the composition comprising agar in addition to a carboxyvinyl polymer as thickeners showed better moisturizing effect than the composition comprising only a carboxyvinyl polymer as a thickener. While the composition of Comparative Example 2 comprises moisturizers of isopropyl myristate and propylene glycol, the composition of the present invention does not comprise any moisturizer. Nevertheless, the composition of Example 1 of the present invention showed better moisturizing effect.

Industrial Applicability

The microbicidal and antiseptic composition of the present invention can be preferably used not only as a microbicidal and antiseptic composition for general household or business use but also as a microbicidal and antiseptic composition for frequent use in hospitals since the composition has resistance to dripping, excellent feel, and good moisturizing effect.

The invention claimed is:

1. A microbicidal and antiseptic composition, which comprises the following (a), (b) and (c):
   (a) at least an alcohol selected from the group consisting of ethanol and isopropanol;
   (b) at least a carboxyvinyl polymer selected from the group consisting of a polyacrylic acid, a polyacrylate, a copolymer of a polyacrylic acid and a polyacrylic acid alkyl ester, and a copolymer of a polyacrylate and a polyacrylic acid alkyl ester; and
   (c) a low-strength agar having a jelly strength of 10 to 250 g/cm$^2$ as measured in a gel state at a concentration of 1.5% (w/w),
   wherein the alcohol content relative to the whole composition is 40 to 95% (v/v), and
   wherein the agar content relative to the whole composition is 0.01 to 1% (w/v).

2. The microbicidal and antiseptic composition according to claim 1, wherein the low-strength agar is obtained by cleaving molecules of natural agar by acid treatment, alkali treatment or heat treatment.

3. The microbicidal and antiseptic composition according to claim 1, wherein the carboxyvinyl polymer content relative to the whole composition is 0.01 to 4% (w/v).

4. The microbicidal and antiseptic composition according to claim 1, which further comprises at least one member selected from the group consisting of cellulose and a cellulose derivative.

5. The microbicidal and antiseptic composition according to claim 1, which further comprises at least one member selected from the group consisting of higher aliphatic alcohols having 12 to 22 carbon atoms.

6. A microbicidal and antiseptic method, which comprises applying the composition according to claim 1 to a hand.

7. The microbicidal and antiseptic composition according to claim 1, which further comprises hydroxypropyl cellulose.

8. The microbicidal and antiseptic composition according to claim 1, which further comprises an alkanolamine.

9. The microbicidal and antiseptic composition according to claim 8, wherein the alkanolamine is diisopropanolamine.

10. The microbicidal and antiseptic composition according to claim 1, which further comprises hydroxypropyl cellulose and diisopropanolamine.

11. A microbicidal and antiseptic composition, which comprises the following (d), (e), (f), (g), (h) and (i):
    (d) ethanol at a concentration of 78.9%(v/v),
    (e) carboxyvinyl polymer,
    (f) hydroxypropyl cellulose at a concentration of 0.05%(w/v),
    (g) low-strength agar having a jelly strength of 10 to 250 g/cm$^2$ as measured in a gel state at a concentration of 1.5% (w/w),
    (h) diisopropanolamine, and
    (i) water.

12. A method for sterilizing or disinfecting a hand, which comprises:
    a step of applying a composition to the hand, and
    a step of rubbing the composition into the hand to sterilize or disinfect the hand,
    wherein the composition comprises the following (a), (b) and (c):
    (a) at least an alcohol selected from the group consisting of ethanol and isopropanol;
    (b) at least a carboxyvinyl polymer selected from the group consisting of a polyacrylic acid, a polyacrylate, a copolymer of a polyacrylic acid and a polyacrylic acid alkyl ester, and a copolymer of a polyacrylate and a polyacrylic acid alkyl ester; and (c) a low-strength agar having a jelly strength of 10 to 250 g/cm² as measured in a gel state at a concentration of 1.5% (w/w),
wherein the alcohol content relative to the whole composition of the composition is 40 to 95% (v/v), and
wherein the agar content relative to the whole composition of the composition is 0.01 to 1% (w/v).

13. The method for sterilizing or disinfecting a hand according to claim 12, wherein 0.5 to 3 mL of the composition is applied to the hand at a time.

14. A method for providing smoothness and resistance to dripping to a microbicidal and antiseptic composition, comprising
adding a low-strength agar having a jelly strength of 10 to 250 g/cm² as measured in a gel state at a concentration of 1.5% (w/w) to a first microbicidal and antiseptic composition to obtain a second microbicidal and antiseptic composition having smoothness and resistance to dripping,
wherein the first microbicidal and antiseptic composition comprises the following (a) and (b):
(a) at least an alcohol selected from the group consisting of ethanol and isopropanol; and
(b) at least a carboxyvinyl polymer selected from the group consisting of a polyacrylic acid, a polyacrylate, a copolymer of a polyacrylic acid and a polyacrylic acid alkyl ester, and a copolymer of a polyacrylate and a polyacrylic acid alkyl ester,
wherein the alcohol content of the second microbicidal and antiseptic composition is 40 to 95% (v/v), and
wherein the agar content of the second microbicidal and antiseptic composition is 0.01 to 1% (w/v).

* * * * *